(12) United States Patent
Plettner et al.

(10) Patent No.: US 11,540,515 B2
(45) Date of Patent: Jan. 3, 2023

(54) USE OF DIALKOXYBENZENES FOR CONTROL OF HONEY BEE MITE VARROA DESTRUCTOR

(71) Applicants: Simon Fraser University, Burnaby (CA); The State of Israel Ministry of Agriculture & Rural Development Agricultural Research Organization, Rishon Lezion (IL)

(72) Inventors: Erika Plettner, Port Moody (CA); Victoria Soroker, Misgav Dov (IL)

(73) Assignees: Simon Fraser University, Burnaby (CA); The State of Israel Ministry of Agriculture & Rural Development Agricultural Research Organization, Rishon Lezion (IL)

( * ) Notice: Subject to any disclaimer, the term of this patent is extended or adjusted under 35 U.S.C. 154(b) by 0 days.

(21) Appl. No.: 17/257,844

(22) PCT Filed: Jun. 28, 2019

(86) PCT No.: PCT/CA2019/050908
§ 371 (c)(1),
(2) Date: Jan. 4, 2021

(87) PCT Pub. No.: WO2020/000111
PCT Pub. Date: Jan. 2, 2020

(65) Prior Publication Data
US 2021/0289780 A1 Sep. 23, 2021

Related U.S. Application Data

(60) Provisional application No. 62/692,515, filed on Jun. 29, 2018.

(51) Int. Cl.
*A01N 31/14* (2006.01)
(52) U.S. Cl.
CPC .................................. *A01N 31/14* (2013.01)
(58) Field of Classification Search
CPC ....................................................... A01N 31/14
See application file for complete search history.

(56) References Cited

U.S. PATENT DOCUMENTS

| | | |
|---|---|---|
| 9,497,963 B2 | 11/2016 | Plettner et al. |
| 2010/0160451 A1 | 6/2010 | Plettner et al. |
| 2016/0152538 A1 | 6/2016 | Plettner et al. |

FOREIGN PATENT DOCUMENTS

| | | |
|---|---|---|
| WO | 2015143436 A | 10/2015 |

OTHER PUBLICATIONS

Supplementary Search Report dated Mar. 17, 2022, issued in related European Application No. 19825043.3, 14 pages.

(Continued)

*Primary Examiner* — Snigdha Maewall
(74) *Attorney, Agent, or Firm* — Christensen O'Connor Johnson Kindness PLLC

(57) ABSTRACT

The present disclosure provides acaricidal compounds, i.e. compounds 3c {3,6}, 3c {4,6}, 3c {3, 3}, 3c {4,3} and 3c {6,6}, that are effective in killing *Varroa destructor* mites while being harmless to honey bees.

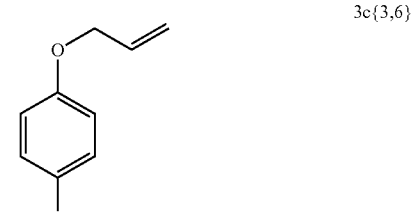

3c{3,6}

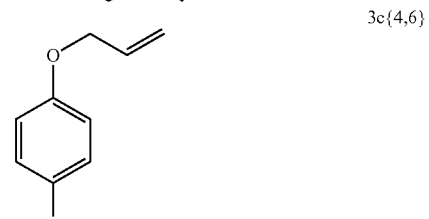

3c{4,6}

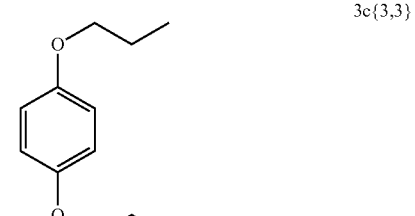

3c{3,3}

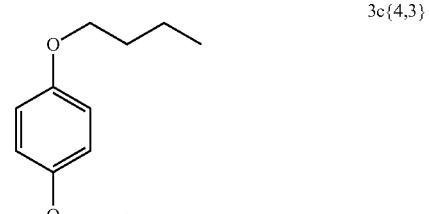

3c{4,3}

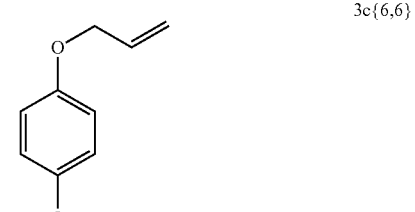

3c{6,6}

20 Claims, 11 Drawing Sheets

(56) References Cited

OTHER PUBLICATIONS

Eliash, N., et al., "Can We Disrupt the Sensing of Honey Bees by the Bee Parasite *Varroa destructor*," PLOS One: vol. 9(9), Sep. 2014, 13 pages.
Plettner, E., et al.,"The chemical ecology of host-parasite interaction as a target of Varroa destructorcontrol agents," Apidologie (2017) 48:78-92.
Ebrahimi, P., et al.,"Partition, sorption and structure activity relation study of dialkoxybenzenes that modulate insect behavior," J. Chemosphere 93 (2013) 54-60.
Paduraru, P.M, et al.,"Synthesis of Substituted Alkoxy Benzene Minilibraries. for the Discovery of New Insect Olfaction ar Gustation Inhibitors," Journal Comb. Chem. (2008): 10, 123-134.
Akhtar, Y., et al.,"Screening of Dialkoxybenzenes and Disubstituted Cyclopentene Derivatives against the Cabbage Looper, *Trichoplusia ni*, for the Discovery of New Feeding and Oviposition Deterrents," J. Agric. Food Chem. (2007): vol. 55(25), 10323-10330.
Singh, N.K, et al., "Effect of the insect feeding deterrent 1-allyloxy-4-propoxybenzene on olfactory responses and host choice of Varroa destructor," Apidologie (2020) 51:1133-1142.

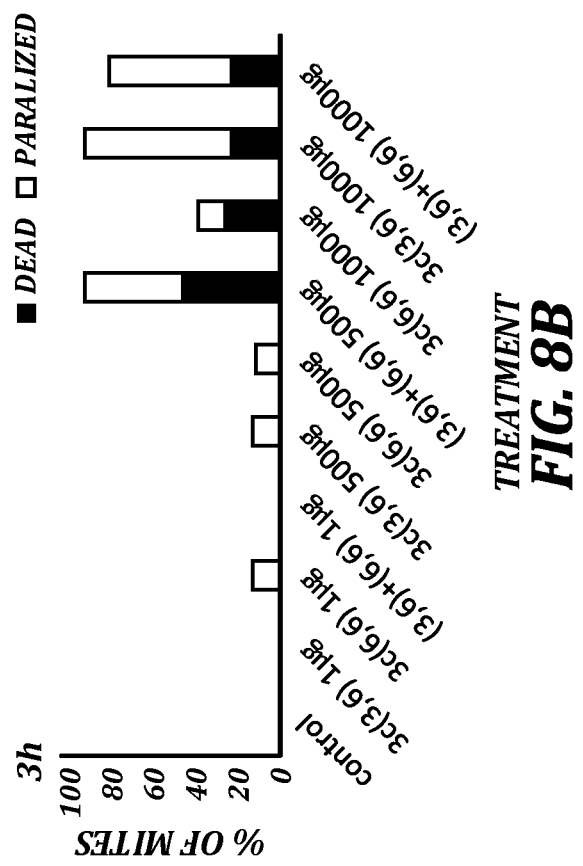
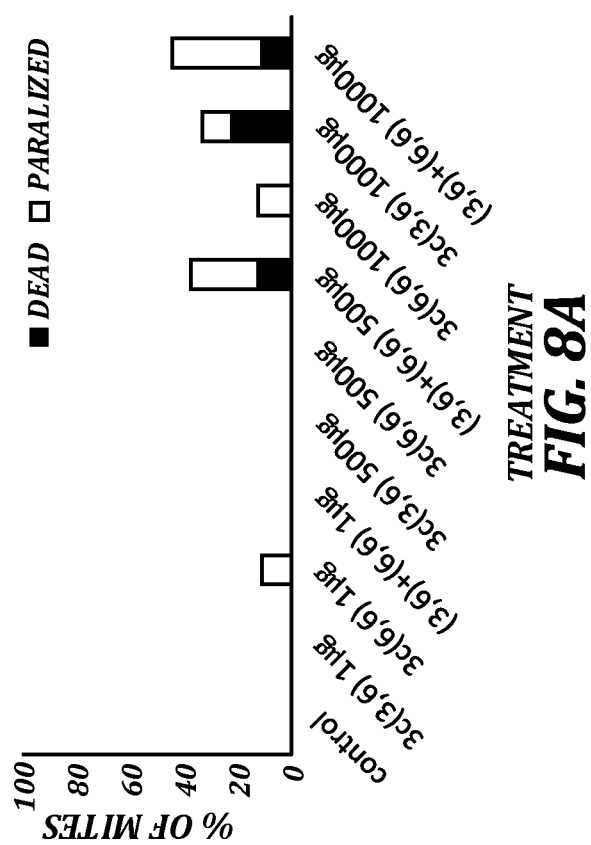
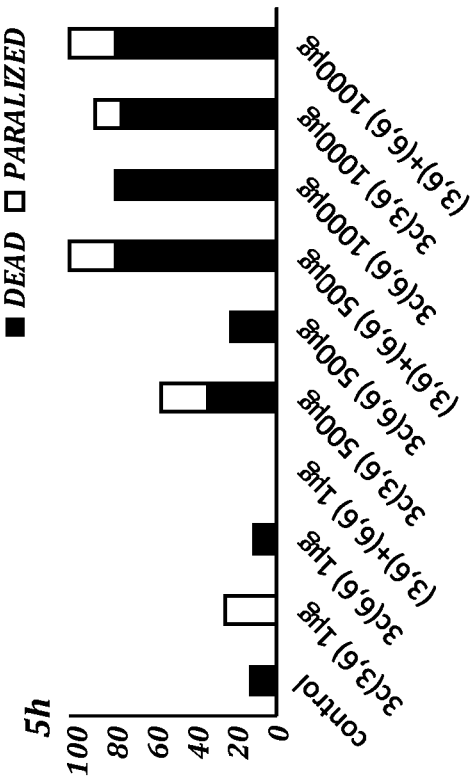

USE OF DIALKOXYBENZENES FOR CONTROL OF HONEY BEE MITE VARROA DESTRUCTOR

CROSS-REFERENCES TO RELATED APPLICATIONS

This application is a National Stage of International Application No. PCT/CA2019/050908, filed Jun. 28, 2019, which claims the benefit Provisional Application No. 62/692,515, filed Jun. 29, 2018, the disclosure of each of which incorporated herein by reference in its entirety.

BACKGROUND

The ectoparasitic mite *Varroa destructor* is at the top of the list of risk factors for honey bee colony losses. This mite of honey bees originally developed in association with the Eastern honey bee *Apis cerana*, but since the beginning of the last century, mites are spreading worldwide among the colonies of the European honey bee *A. mellifera*, vectoring highly pathogenic viruses.

Failure of conventional chemical acaricides in *Varroa* control is due to widespread resistance. Also, negative effects of widely used acaricides on bees are driving the search for more sustainable and environmentally compatible methods of *Varroa* control.

The life cycle of *Varroa* is totally dependent on that of its host, the honeybee, and is divided into two stages: phoretic and reproductive. Briefly, in the phoretic stage, mites tend to attach to adult bees and feed on their haemolymph, whereas in the reproductive stage, mites reproduce within the capped brood cells feeding on pupal haemolymph. Between these phases *Varroa* move freely on the surface of the comb.

Laboratory bioassay by several researchers proved that *Varroa* mites are using chemical cues for discriminating between bees from different task groups and to prefer a nurse over a forager bee. These cues are detected by a chemosensory organ localized on mites' forelegs. At the same time, colonial activities of honeybees are also coordinated mainly by chemical cues detected by their antennae.

New acaricidal compounds are needed to control *Varroa destructor* infestations. The present disclosure seeks to fulfill this need and provides further related advantages.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, the present disclosure features a method of killing *Varroa destructor*, including: applying an effective amount of a first acaricidal compound selected from

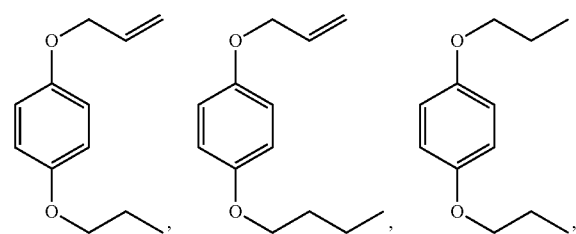

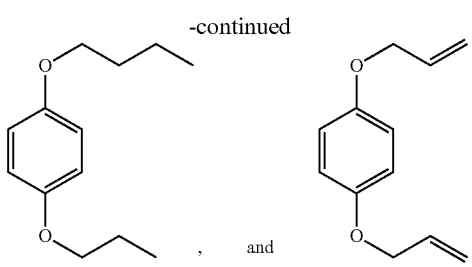

to a *Varroa destructor*-infected honey bee population for a period of at least 3 hours (e.g., at least 12 hours, at least 24 hours, at least 48 hours); and killing the *Varroa destructor* by an amount of at least 50%.

In another aspect, the present disclosure features a method of killing *Varroa destructor*, including: applying an effective amount of a compound of Formula

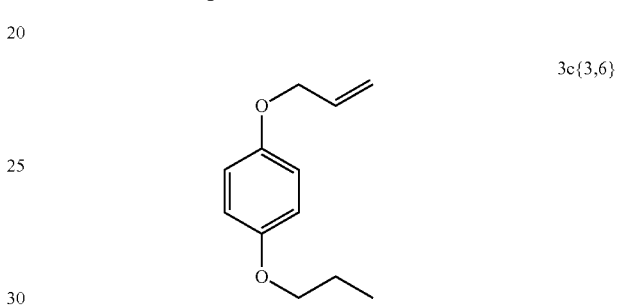

to a *Varroa destructor*-infected honey bee population for a period of at least 3 hours (e.g., at least 12 hours, at least 24 hours, at least 48 hours); and killing the *Varroa destructor* by an amount of at least 50%.

DESCRIPTION OF THE DRAWINGS

The foregoing aspects and many of the attendant advantages of this disclosure will become more readily appreciated as the same become better understood by reference to the following detailed description, when taken in conjunction with the accompanying drawings, wherein:

FIG. 8A is a graph of mite death and paralysis when exposed to embodiments of the compounds of the present disclosure at 1 hour exposure.

FIG. 8B is a graph of mite death and paralysis when exposed to embodiments of the compounds of the present disclosure at 3 hours exposure.

FIG. 8C is a graph of mite death and paralysis when exposed to embodiments of the compounds of the present disclosure at 5 hours exposure.

DETAILED DESCRIPTION

Figure 1:
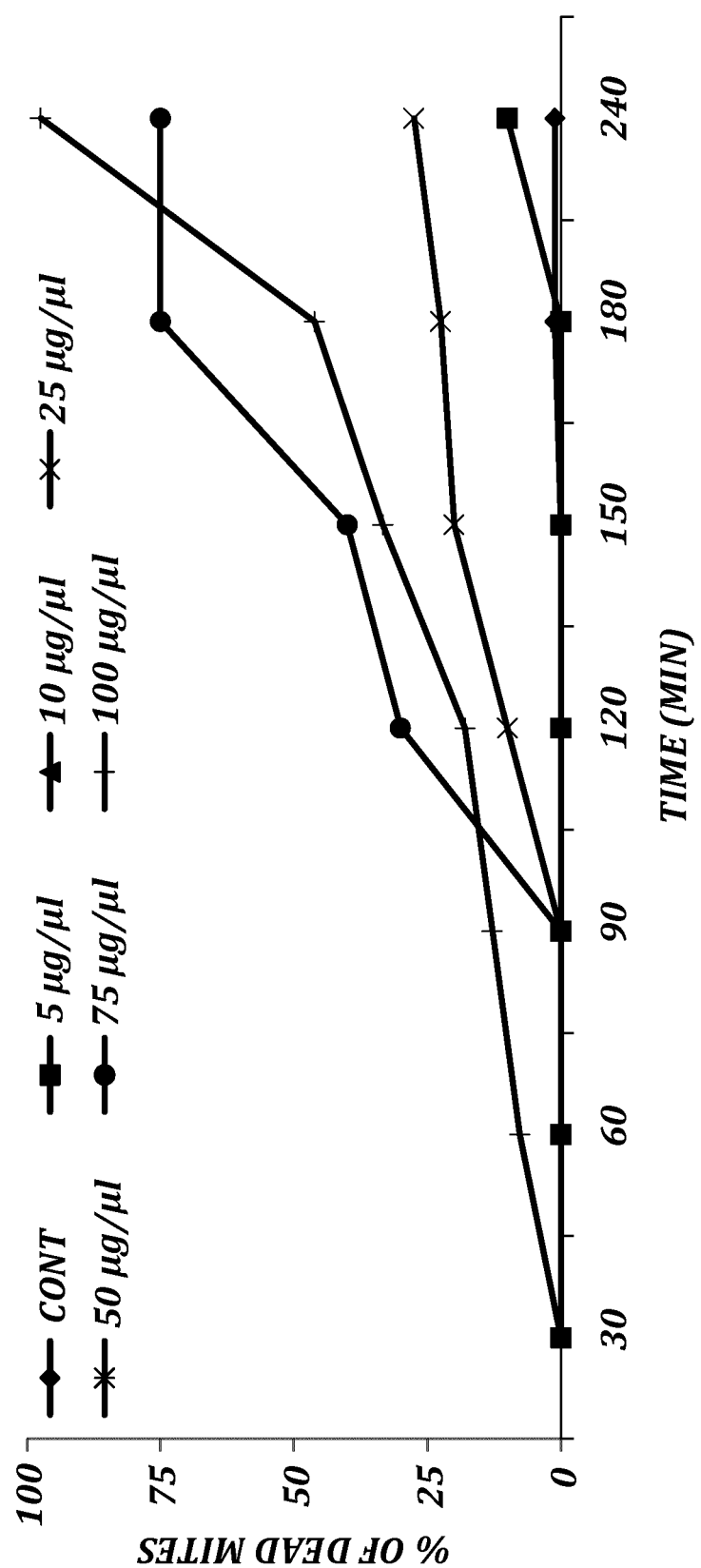
FIG. 1 is a graph showing dose-dependent acaricidal effect of embodiments of compounds of the present disclosure (CONT: control).

The present disclosure provides acaricidal compounds that are effective in killing *Varroa destructor* mites, while being harmless to honey bees.

In some embodiments, the present disclosure features a method of killing *Varroa destructor*, including applying an effective amount of a first acaricidal compound selected from

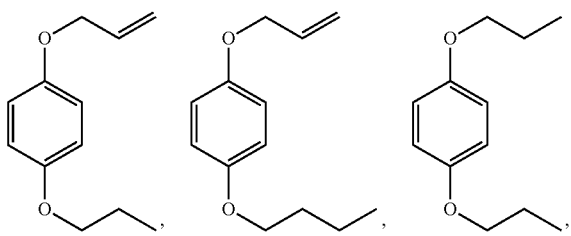

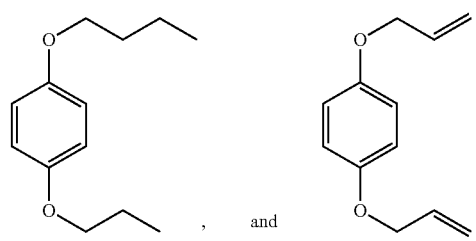

to a *Varroa destructor*-infected honey bee population for a period of at least 3 hours (e.g., at least 12 hours, at least 24 hours, or at least 48 hours); and killing the *Varroa destructor* by an amount of at least 50%.

In some embodiments, the effective amount of the first acaricidal compound is applied to a *Varroa destructor*-infected honey bee population for a period of 14 days or more (e.g., 18 days or more, 20 days or more, 22 days or more, or 24 days or more) and/or 28 days or less (e.g., 24 days or less, 22 days or less, 20 days or less, or 18 days or less). In some embodiments, the effective amount of the first acaricidal compound is applied to a *Varroa destructor*-infected honey bee population for a period of 14 to 28 days.

In some embodiments, the first acaricidal compound selectively kills *Varroa destructor*. In some embodiments, the first acaricidal compound does not kill or injure honey bees.

In some embodiments, the effective amount of the first acaricidal compound is from 50 to 100 micrograms per 5 to 10 *Varroa destructor* mites. In some embodiments, an effective amount of the first acaricidal compound provides 5 ng or more (e.g., 10 ng or more, 15 ng or more, or 20 ng or more) and/or 25 ng or less (e.g., 20 ng or less, 15 ng or less, or 10 ng or less) of the first acaricidal compound per $cm^3$ of a headspace volume in a honey bee colony enclosure over a period of 3 hours or more (e.g., 6 hours or more, 12 hours or more, 1 day or more, 7 days or more, 14 days or more, or 21 days or more) and/or 28 days or less (e.g., 21 days or less, 14 days or less, 7 days or less, 1 day or less, 12 hours or less, or 6 hours or less). As used herein, the term "headspace" in a honey bee colony enclosure refers to the unfilled space surrounding honey bees in a honey bee colony enclosure. As used herein, "headspace" as it relates to an insect refers to the air space that surrounds a given insect (e.g., the sensory organs of a given insect). In certain embodiments, applying the effective amount of the first acaricidal compound to a *Varroa destructor*-infected honey bee population includes applying the first acaricidal compound (e.g., in the form of a solid, for example, in a permeable container such as a sachet; in the form of a solution on a substrate; or in the form of a solid coating on a substrate) to a honey bee colony enclosure. The first acaricidal compounds of the present disclosure can be volatile at room temperature (e.g., 22° C.) at 1 atm. The first acaricidal compounds can condense on a surface in a bee colony enclosure. In some embodiments, the first acaricidal compounds can be used as a fumigant. As used herein, a fumigant refers to a substance that evaporates and exerts its effect both at the site of application and at other nearby sites where the vapors diffuse to and/or condense. In some embodiments, the first acaricidal compound can permeate throughout a bee colony enclosure, but does not diffuse through solids and liquids in an amount that is harmful to bees.

In certain embodiments, the first acaricidal compound is

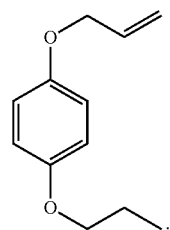

In certain embodiments, the first acaricidal compound is

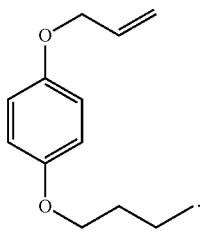

In certain embodiments, the first acaricidal compound is

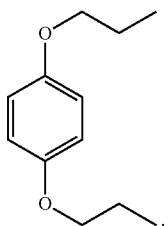

In some embodiments, the first acaricidal compound is

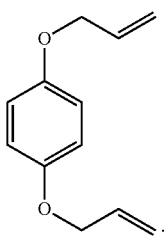

The present disclosure also features a method of killing *Varroa destructor*, including: applying an effective amount of a compound of Formula

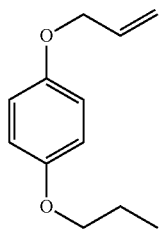

3c{3,6} to a *Varroa destructor*-infected honey bee population for a period of at least 3 hours (e.g., at least 12 hours, at least 24 hours, at least 48 hours); and killing the *Varroa destructor* by an amount of at least 50%.

In some embodiments, the effective amount of the compound of Formula 3c{3,6} is applied to a *Varroa destructor*-infected honey bee population for a period of 14 days or more (e.g., 18 days or more, 20 days or more, 22 days or more, or 24 days or more) and/or 28 days or less (e.g., 24 days or less, 22 days or less, 20 days or less, or 18 days or less). In some embodiments, the effective amount of the compound of Formula 3c{3,6} is applied to a *Varroa destructor*-infected honey bee population for a period of 14 to 28 days.

In some embodiments, the effective amount of the compound of Formula 3c{3,6} is from 50 to 100 micrograms per 5 to 10 *Varroa destructor* mites. In some embodiments, an effective amount of the compound of Formula 3c{3,6} provides 5 ng or more (e.g., 10 ng or more, 15 ng or more, or 20 ng or more) and/or 25 ng or less (e.g., 20 ng or less, 15 ng or less, or 10 ng or less) of the compound per $cm^3$ of a headspace volume in a honey bee colony enclosure over a period of 3 hours or more (e.g., 6 hours or more, 12 hours or more, 1 day or more, 7 days or more, 14 days or more, or 21 days or more) and/or 28 days or less (e.g., 21 days or less, 14 days or less, 7 days or less, 1 day or less, 12 hours or less, or 6 hours or less). The compound of Formula 3c{3,6} can be applied in the form of a solid, for example, in a permeable container such as a sachet; or in the form of a liquid, for example, on a substrate, to a honey bee colony enclosure.

In some embodiment, the compound having Formula 3c{3,6} selectively kills *Varroa destructor*. In certain embodiments, the compound having Formula 3c{3,6} does not kill or injure honey bees.

In some embodiments, the compounds of the present disclosure induce paralysis in the *Varroa destructor* when an effective amount of one or more compounds is applied to a *Varroa destructor*-infected honey bee population for a period of at least 3 hours (e.g., at least 12 hours, at least 24 hours, at least 48 hours), and/or for a period of 14 days or more (e.g., 18 days or more, 20 days or more, 22 days or more, or 24 days or more) and/or 28 days or less (e.g., 24 days or less, 22 days or less, 20 days or less, or 18 days or less). As used herein, paralysis refers paralysis to a condition wherein the mite is no longer able to move productively, moves its legs in an uncoordinated manner, is unable to right itself if on its back, and/or fails to move altogether.

In some embodiments, the compounds of the present disclosure have a *Varroa destructor* EC50 of about 5 μg or more (e.g., 25 μg or more, 50 μg or more, 100 μg or more, 200 μg or more, 300 μg or more, 400 μs or more, 500 μg or more, or 600 μg or more) and/or 750 μg or less (e.g., 600 μs or less, 500 μg or less, 400 μg or less, 300 μs or less, 200 μg or less, 100 μg or less, 50 μs or less, or 25 μg or less).

In some embodiments, the methods above further include applying a second acaricide, such as an organic acid (e.g., formic acid and/or oxalic acid). In some embodiments, the methods further include applying a second acaricide, such as thymol, eucalyptol, camphor, menthol, and/or methyl salicylate.

In some embodiments, the methods above further include applying a compound that alters host choice behavior of *Varroa* mites, such as 1,3-dialkoxybenzene, 1-ethoxy-5-(2'ethoxyethyl)cyclopent-2-ene, and/or 1-butoxy-5-(2'methoxyethyl)cyclopent-2-ene.

The Examples below demonstrate the acaricidal effects of the compounds of the present disclosure.

EXAMPLES

Example 1. Effect of 1-allyloxy-4-propoxybenzene on Olfactory Responses of *Varroa destructor*

Electrophysiology was shown to be a reliable technique for identification of chemosensory disrupting compounds for *Varroa*. Using this technique, dialkoxybenzenes and ethers of 5(2'-hydroxyethyl) cyclopent-2-en-1-ol and the widely used insect repellent, N,N-diethyl-meta-toluamide (DEET) that disrupt *Varroa* host sensing, were evaluated. The identified compounds were found effective in disruption of host selection by *Varroa*, but their modes of action were different. While dialkoxybenzene and ethers switched the preference of *Varroa* towards foragers without affecting the ability of *Varroa* to reach a bee, DEET specifically reduced the ability of mites to reach a bee without affecting the preference. Moreover, DEET was not found to affect chemosensing and behavior of honey bees. This specificity and efficacy of DEET made it an attractive candidate for *Varroa* control. However, negative effects of DEET are also well known and, in particular, it inhibits the activity of a key central nervous system enzyme, acetylcholinesterase in both insects and mammals.

The ectoparasitic *Varroa destructor* (Anderson and Trueman) (Acar: Varroidae) is a major threat for the honey bee, *Apis mellifera* L. *Varroa* are arrested by honey bee-produced compounds, as well as cues from the general colony environment. Here, 1-allyloxy-4-propoxybenzene, 3c{3,6}, a feeding deterrent of Lepidoptera larvae and a repellent of mosquitoes of similar activity to DEET, was tested for its ability to disrupt *Varroa* host chemosensing. Its effect on *Varroa* mites was evaluated by electrophysiological and behavioral bioassays. Its effect on honeybee chemosensing was also assessed. Compound 3c{3,6} is sensed by honey bees, but its detection by *Varroa* is not clear.

The electrophysiological study showed that 3c{3,6} decreases the *Varroa* foreleg responses towards head space odor of nurse bees. On the other hand, the response of honey bee antennae towards nurse bee head space odor was not affected. Consistently with electrophysiological studies, in presence of 3c{3,6}, the ability of *Varroa* to reach any host decreased at the end of the experiment. No lethal effect to the honey bees was recorded. These data indicated that 3c{3,6} affects the peripheral olfactory system of *Varroa* by disrupting of chemical recognition process.

Materials

One experimental apiary was maintained at ARO (Volcani Center, Bet Dagan, Israel). All the bee colonies were kept in standard wooden "Langstroth" hives fitted with a screen bottom board. The hives were maintained without any treatment against *Varroa*, and received seasonal sugar feed. One hive was maintained in Port Moody, B. C., Canada.

Female adults *Varroa* mites were collected directly from emerging bees, using fine tweezers and a fine paint brush. All collected *Varroa* were kept on a moistened filter paper at room temperature until used or not more than 3 hours.

Nurse and foragers bees were collected for the experiments. Bees observed leaning into brood cells were regarded as nurse bees, whereas pollen foragers carrying pollen loads, were collected from the entrance of the hive according to Elaish et al (2014). The bees were killed by freezing at 20° C., for 1 hour. Prior to a behavioral bioassay, the pollen loads were thoroughly removed from forager bees by using forceps or paint brush under stereo microscope. Nurse bees free from *Varroa* were used as taken from the hive.

Compound 3c{3,6} was synthesized from 1,4-dihydroquinone per literature methods. All chemicals were of the highest available grade, and the product was checked by nuclear magnetic resonance and gas-chromatography-mass spectrometry (GC-MS) and found to be pure.

In the electroantennography (EAG), the *Varroa* foreleg or bee antennae were used for the assay. The organs were stimulated by puffs of nurse honeybee odor, or clean air (control). Briefly, once a foreleg or bee antenna preparation was found responsive to a positive stimulus, the tested chemical was blown over the leg/antenna with or without positive stimuli. Headspace of five nurse bees was used as a positive stimulus. This stimuli were selected for *Varroa* following the procedure described, for example, in Eliash, N. et al., (2014) PLoS One, (2014) 9(12): e116127, incorporated herein by reference in its entirety, and following dose response tests on nurse antennae challenged with headspace of 1, 5 and 10 nurse or forager bees. Electrophysiological responses of isolated *Varroa* foreleg and bee antennae were recorded using Synthech equipment, and the order of stimuli was as explained in Singh, K. N. et al., (2014) Apidologie, 46: 380-391, incorporated herein by reference in its entirety. The response amplitude was recorded for each stimulus and normalized relative to air.

Functional activity of the compound was performed using choice bioassay. Briefly, in the presence of the synthetic compound or solvent as a control, the mites were given a choice of two bees (a forager and a nurse) in a petri dish (90 mm diameter and 17 mm deep glass). The movement of *Varroa* and its host preference were monitored at every hour for 3 hours. These tests showed that in the presence of compound the mites hardly reach any bee.

Evaluation of Acaricidal Effect

The effect of the compounds was checked in free moving-mites freshly collected from the bottom board using fine paint brush. All collected *Varroa* were kept on emerging bees at room temperature until the experiment.

Compounds (code-labeled, Table 1) were prepared in hexane:ethyl acetate (1:1) in 10 mM concentration according to instructions. Dilutions only of compound "A" was prepared. As no miticidal effect was seen at any concentration, the other compounds were tested at higher concentration at two doses, 10 µl (=100 nmol) and 30 µl (=300 nmol) volumes; accordingly control treatment of mixture hexane:ethyl acetate (1:1) was implemented. This setup enabled the testing of all the compounds and to save the mites.

The assay was conducted in glass petri dish (90 mm diameter and 17 mm deep glass) containing moistened filter paper. Five emerging bees loaded with two *Varroa* mites were put into each plate. The bees were provided with candy (60% of pollen and 40% sugar). 10 µl or 30 µl volume of each compound or control mix was placed on Parafilm paper (5×5 cm) on the plates cover. The falling mites and their activity were noted at every 30-60 min intervals for 4 hours, and after an additional 20 hours.

The effect of different compounds on mites survival after 24 hours is presented in Table 1. During the experiment, in the first 4 hours all the treated group of mites were alive, however at the end of 24 h, some compounds at the highest amount tested (30 µl) showed clear acaricidal effect. In particular these were compounds M, A, H and F. Other somewhat effective chemicals were N and L. In control and other treatment groups (C,G,M) the mites occasionally fell off bees but reattached quickly and most were on bees by the end of the experiment.

TABLE 1

The effect of 15 chemicals on mite survival. The data are percentages of mites per treatment. The number of mites are marked in brackets for each treatment.

| | | | % of surviving mites 24 h post treatment | |
|---|---|---|---|---|
| Treatment | Code | Amount µg/µl | 10 µl [a,b] (100 nmol) | 30 µl (300 nmol) |
| Control [a] | | | 80 (40) | 100 (60) |
| 3c{3,6} (1-allyloxy-4-propoxybenzene) | A | 19.2 | 100 (20) | 7.5 (40) |
| 3b{3,6} (1-allyloxy-3-propoxybenzene) | B | 19.2 | 95 (20) | 90 (20) |
| 3a{3,6} (1-allyloxy-2-propoxybenzene) | C | 19.2 | 85 (20) | 100 (20) |
| 3c{1,6} (1-(allyloxy)-4-methoxybenzene) | D | 16.4 | 95 (20) | 95 (20) |
| 3c{2,6} (1-(allyloxy)-4-ethoxybenzene) | E | 17.8 | 90 (20) | 80 (20) |
| 3c{4,6} (1-(allyloxy)-4-butoxybenzene) | F | 20.6 | 100 (20) | 33 (30) |
| 3c{n5,6} (1-(allyloxy)-4-(pentyloxy)benzene) | G | 22 | 90 (20) | 100 (20) |
| 3c{3,3} (1,4-dipropoxybenzene) | H | 19.4 | 80 (20) | 22.5 (40) |
| 3c{4,4} (1,4-dibutoxybenzene) | I | 22.2 | 95 (20) | 100 (20) |
| 3c{3,n5} (1-(pentyloxy)-4-propoxybenzene) | J | 22.2 | 95 (20) | 95 (20) |
| 3c{4,n5} (1-butoxy-4-(pentyloxy)benzene) | K | 23.6 | 35 (20) [c] | 95 (40) |
| 3c{4,3} (1-butoxy-4-propoxybenzene) | L | 10.8 | 95 (20) | 45 (20) |
| 3c{6,6} (1,4-bis(allyloxy)benzene) | M | 19.2 | 55 (20) | 0 (40) |
| thymyl formate | N | 17.8 | 90 (20) | 55 (40) |
| dithymyloxalate | O | 35.4 | 80 (20) | 90 (20) |

[a] The compound was delivered as a solution in hexane at 10 nmol/µL.
[a,b] The controls received the same volume of pure solvent as the treatments, 10 µL and 30 µL, respectively.
[c] mites drowned in bee food

Example 2. Evaluation of the Acaricidal Effect of 3c{3,6}

The experiments were conducted in glass petri dish under control environment as described above in Example 1. Two sets of experiments were conducted compound 3c{3,6}:
1. Dose response assay on 10 mites per plate. Doses are in microgram.
2. Assay on mites phoretic on young bees. In this experiment 100 microgram/µl solution and its dilutions were used. Two mites were placed on each living young bee.

In the first assay the percentage of dead mites as function of exposure time to different quantities of the compound was measured. As can be seen in FIG. 1, the acaricidal effect is clear and it is dose dependent. The effective doses are relatively high.

Figure 2:
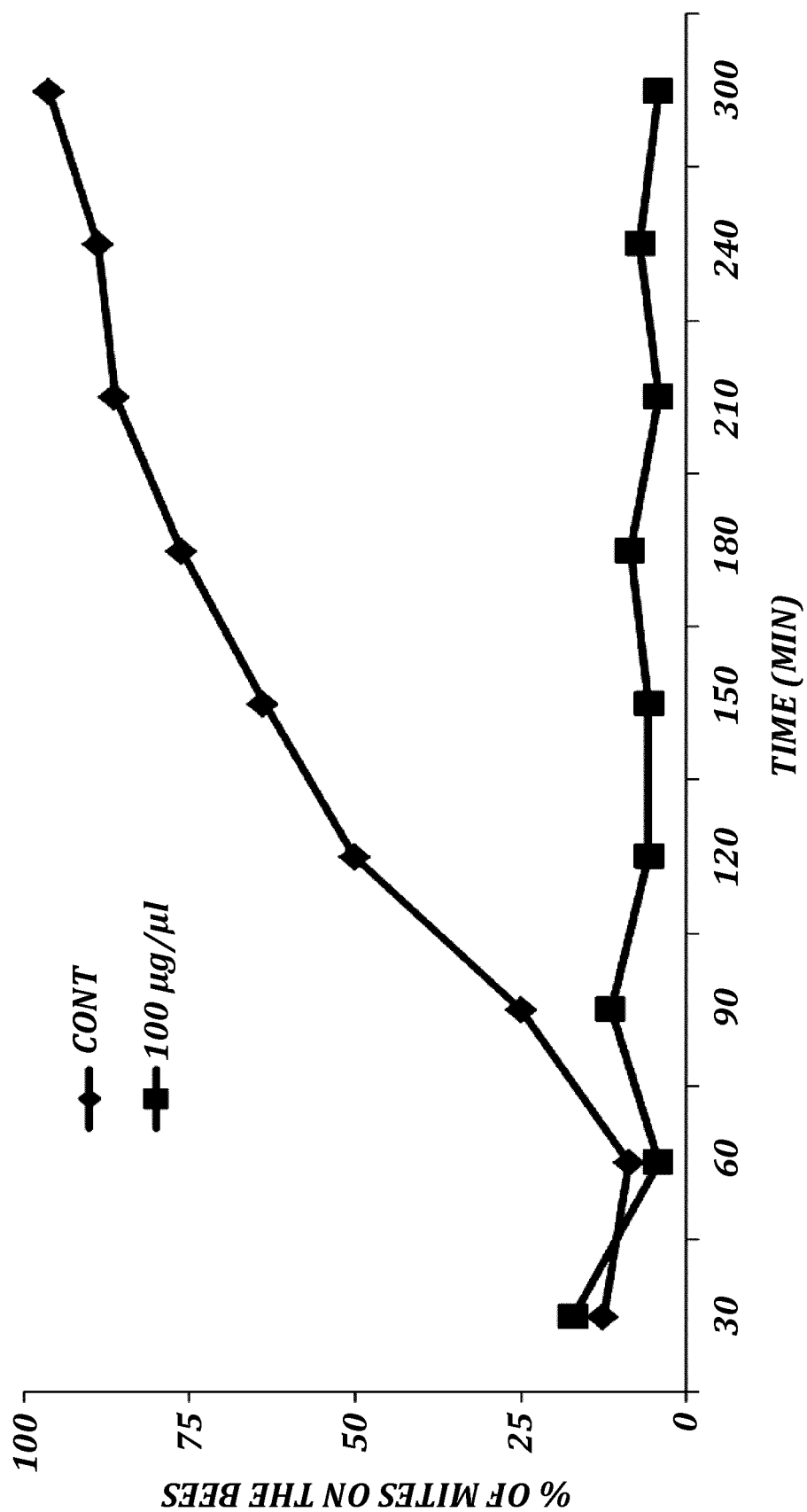
FIG. 2 is a graph showing the mite-fall effect of an embodiment of a compound of the present disclosure.

In the second assay the percentage of mites dropping from bees as function of time was measured (FIG. 2). The results were dramatic: by the end of experiment the Varroa dropped dead off the bees, while bees in most of the cases remained in perfect shape.

Effect of Compound 3c{3,6} on Bee Mortality

3c{3,6} sensed by smell: Bees were maintained in the classic hoarding cages. The test was conducted on twenty freshly collected bees in hoarding cages as above. The method that was used for screening potentially harmful compounds was as described, for example, in Medrzycki et al., 2013 (J. Apicultural Res. 52 (4): UNSP 52.4.14, http://dx.doi.org/10.3896/IBRA.1.52.4.14, incorporated herein by reference in its entirety. The bees were provided with water and candy at lib. The experiments were conducted in ten sets in the presence of 30 µl of hexane containing 300 µg of the 3c{3,6} compound presented in Parafilm (5×5 cm); 30 µl of pure hexane was used for control. The experimental and control cages were kept in separate incubators at (28-30° C.) and RH (50-70%) and the bee mortality rate was recorded at 24, 48 and 72 hours. Survival of bees in control and treated groups at the end was similar (79-90%).

3c{3,6} provided in sugar solution: The test was conducted on twenty freshly collected bees in hoarding cages as described above. Survival of bees in control and treated group was similar along the experiment (21% and 5% bees died at the end of experiment after 72 hours in control and treated groups respectively). The tested 3c{3,6} compound did not have negative effect on the honeybees. In addition, no differences were apparent in the general behavior of the honeybees. Furthermore, honey bees can ingest compound 3c{3,6} without harm and without increase in mortality.

Example 3. Dose Response of 3c{3,6}

Materials. The experiments were done during the month of August, using bees from a hive in British Columbia. Varroa destructor mites emerged from combs were taken from infested hives. The combs were kept in nucleus boxes at ~23-25° C. Newly emerged bees with mites on them were harvested daily and placed in hoarding cages until they were used in an experiment. Once the first set of combs was older than 9 days, mites were also harvested by opening cells and catching them as they emerged.

Nurse and forager bees were harvested from a healthy hive with very low mite loads using a vacuum for bees. Foragers were taken from the hive entrance, and nurses were taken from combs with brood. Bees for the assays in dishes were frozen at −86° C. initially, then placed at −20° C., and foragers were kept separate from nurses. Bees for cage assays (see below) were kept in hoarding cages with access to sugar syrup.

Mites were harvested from bees in the holding cages using a fine painter's brush. They were held in a Petri dish with a moribund bee as food until the assay dishes with bees were ready.

For paralysis assays, 10 cm glass Petri dishes were used. For the experiment with live bees, Plexiglass hoarding cages with a screened bottom and a fine mesh draped over the ventilation holes were used.

Compounds tested were: 3b{2,2} (1,3-diethoxybenzene), 3c{3,6} (1-allyloxy-4-propoxybenzene) and 3c{6,6} (1,4-diallyloxybenzene).

Paralysis assays. These assays were done in 10 cm glass Petri dishes. A 3×3 cm piece of Parafilm was stuck to the lid of the dish, in the middle. The Parafilm received 10 of hexane, either pure (controls) or with the compound (treatments). The bottom of the dish received one freshly thawed nurse and one freshly thawed forager, placed ~3 cm from the center of the dish. One mite was placed between the nurse and the forager, the lid was closed and groups of dishes were placed in an incubator at 30° C. Humidity levels were kept at around 35-40%.

Observation times were 3 h and 5 h. Mites were scored for whether the mite could move normally, was paralyzed (had difficulty moving) or dead (not moving).

Each assay was done in 5 technical replicates, in two biological replicates. Thus, each biological replicate was scored out of 5.

Experiments were performed in the dishes: i) dose response assays with a single compound at different doses of compound on the Parafilm (1 ng, 10 ng, 100 ng, 1 µg, 10 µg, 100 µg, 1 mg and 10 mg), ii) a screen with six compounds, all at a 1 mg dose, iii) an assay with blends of compounds 3c{3,6} and 3c{6,6}, and iv) one assay without bees (only to check for mite paralysis and death), with compounds 3c{3,6} and 3c{6,6}(pure or 1:1 blend), at 0.5 and 1 mg doses.

Live Bee Assays.

Cage assays. These assays were done with 5 nurses, 5 foragers, and 5 mites (first round) or 5 nurses, 5 foragers, and 10 mites (second round). Nurses were marked with a white queen marking pen, and foragers were marked with a green pen on the thorax. In the first live bee assay mites were marked with a small red marking pen dot; in the second assay mites were not marked.

The assays were done with a 1:1 mixture of 3c{3,6} and 3c{6,6}, along with a blank (solvent only) and a positive control (0.5% oxalic acid given in water). In the first assay, the blend was delivered in two different ways: 1 mM in the drinking water or as a solid (10 mg total) on a slide placed under the mesh, such that bees could not come in direct contact with the compound. In the second assay only the treatment with solid compound evaporating from a slide was given.

Bees had access to hardened fondant candy and water. Cages were kept at 30° C. in an incubator with 35-40% humidity. Observations were made at 2, 24 and 48 hours after setup. Where possible, the number of nurses and foragers that had mites on them was recorded. The number of paralyzed or dead mites, as well as of dead bees was also recorded. Any dead bees were removed from the cage using soft forceps and inspected for mites.

Air (1 mL) was removed from control and treatment cages using a gastight syringe and analyzed by GC-MS on a Varian Saturn 2000 ion trap GC-MS instrument. The full volume (1 mL) was injected. The GC was programmed as follows: 80° C. (5 min), 10° C./min to 250° C. (1 min). The injector was kept at 220° C. The MS had the following program: 0-5 min: acquisition delay, 5-14 min 80-400 amu, 14-16 min 90-200 amu and 16-23 min 80-400 amu. Compounds 3c{3,6} and 3c{6,6} eluted in the middle of the 14-16 min acquisition window. The instrument's response was calibrated with standards of both compounds.

Colony test. One colony of two supers was treated with solid 3c{3,6}, delivered in organza bags. The colony was otherwise healthy (apart from having *Varroa* mites), and the bee cluster reached over both boxes. Above the top box was placed a queen excluder and a top-feeding box. The following treatments were done: i) Day 1: 4×60 mg with bags placed above the cluster in the top box (below the queen excluder) only; ii) After 30 days: 4×60 mg with bags placed above the cluster in the top box (below the queen excluder) only; iii) After an additional 14 days, 4×100 mg with two bags placed on top of the lower box (i.e. between the two boxes) and two bags placed on top of the cluster on the top box (just below the queen excluder) iv) After an additional 7 days, 4×100 mg was added and the bags from the previous week were kept in. On the third treatment two Pasteur pipettes with Porapak (wedged between glass wool plugs in the pipette) were installed, one in the middle of the top cluster, the other on the edge of the cluster. These were removed. The colony was fitted with a screened bottom platform and a white *Varroa* counting drawer underneath the screen. Mites on the counting drawer board were counted every few days.

Porapak cartridges were extracted with hexane:ethyl acetate (4:1) with 40 ng/µL of 1,4-dimethoxybenzene as internal standard. Solvent (5 mL) were drizzled through the Porapak column and the eluate was directed over a bed of silica gel (also packed in a Pasteur pipette). The volume collected was noted (3.7-3.8 mL was recovered).

Paralysis Assays.

Dose Responses

Compounds 3c{3,6} and 3c{6,6} both caused paralysis and eventual death of mites. The $EC_{50}$ for 3c{3,6} for this activity was 41.5 µg of the neat compound on the source (with 95% confidence limits of 5.4 µg and 321 µg), and the $EC_{50}$ for 3c{6,6} was 182 µg of the neat compound on the source (with 95% confidence limits of 45 µg and 734 µg). Thus compound 3c{6,6} was ca. 4× less active than 3c{3,6} with regard to paralysis and death of mites. It is of note that the mites did not come in contact with the compound directly, only with the vapors of the compound.

Figure 3A:
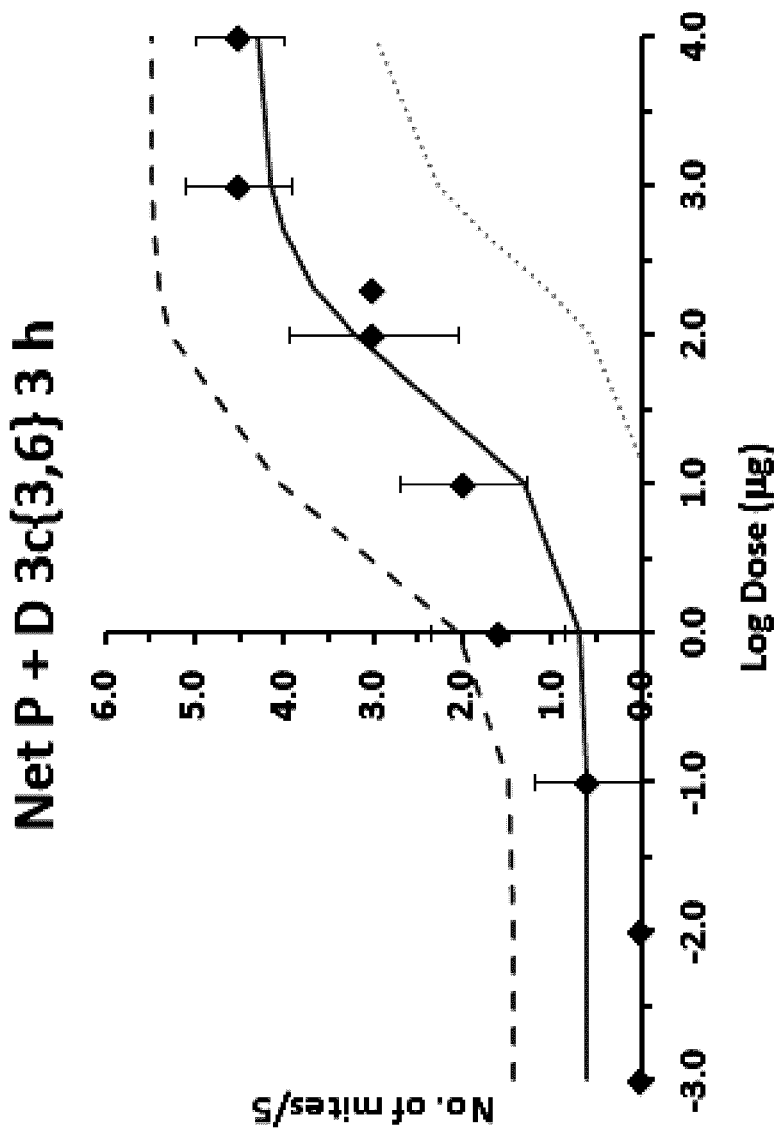
FIG. 3A is a graph of dose responses of net dead or paralyzed mites after 3 h of treatment for an embodiment of a compound of the present disclosure.
Figure 3B:
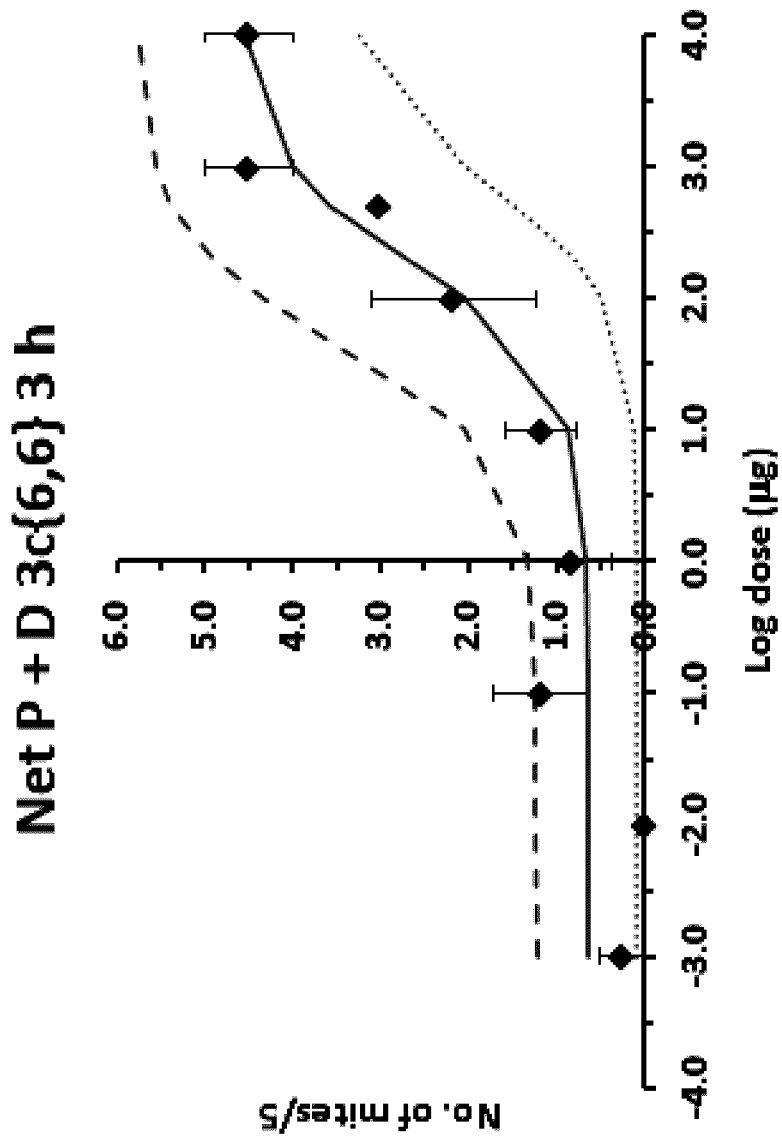
FIG. 3B is a graph of dose responses of net dead or paralyzed mites after 3 h of treatment for an embodiment of a compound of the present disclosure.

FIGS. 3A and 3B show the dose responses of net dead or paralyzed mites after 3 h of treatment. The number of mites plotted represents the dead+paralyzed mites in the treatment minus the dead+paralyzed mites in the solvent control that was paired with treatments in each replicate. FIG. 3A shows the dose response for 1-allyloxy-4-propoxybenzene (3c{3,6}). FIG. 3B shows the dose response for 1,4-diallyloxybenzene (3c{6,6}). Points represent the average of 2-5 replicates per dose±S.E. (for n≥3) or range (for n=2). The solid curve traces the calculated dose response, based on the $EC_{50}$ and the activity range obtained. The dotted curve shows the low activity model, whereas the dashed curve shows the high activity model within the 95% confidence limits.

Screen

Figure 4A:
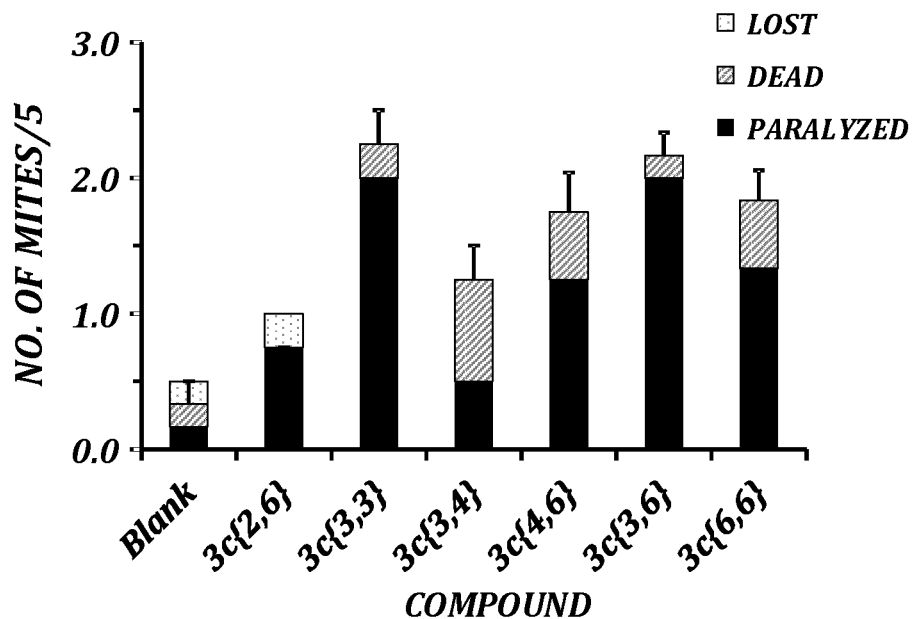
FIG. 4A is a graph of the paralysis, death or loss of mites during assays with embodiments of compounds of the present disclosure.
Figure 4B:
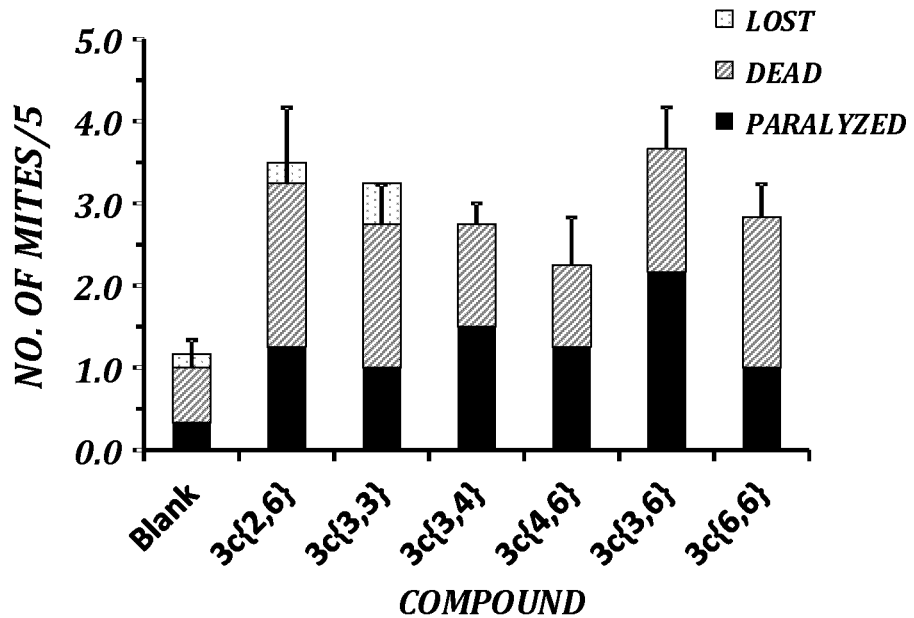
FIG. 4B is a graph of the paralysis, death or loss of mites during assays with embodiments of compounds of the present disclosure.

In order to gain insight into structure-activity relationships, a small screen was done with compounds 3c{2,6}, 3c{3,6}, 3c{4,6}, 3c{3,3}, 3c{3,4} and 3c{6,6}. At 3 h the compounds differed in the amount of paralysis and mite death caused. Compound 3c{2,6} caused little paralysis and some mite losses, possibly due to escape from the dishes. Compounds 3c{3,3} and 3c{3,6} caused the most reliable mite paralysis. Compound 3c{3,4} caused the most death at 3 h (FIG. 4A). At 5 h all the compounds tested caused substantial paralysis and death, compared to the blank (FIG. 4B). Compound 3c{4,6} was slightly less active than compound 3c{3,6}. FIG. 4A shows the paralysis, death or loss of mites during assays with the compounds at 3 h. Bars represent the average of 4 replicates±S. E.

Blends

Figure 5:
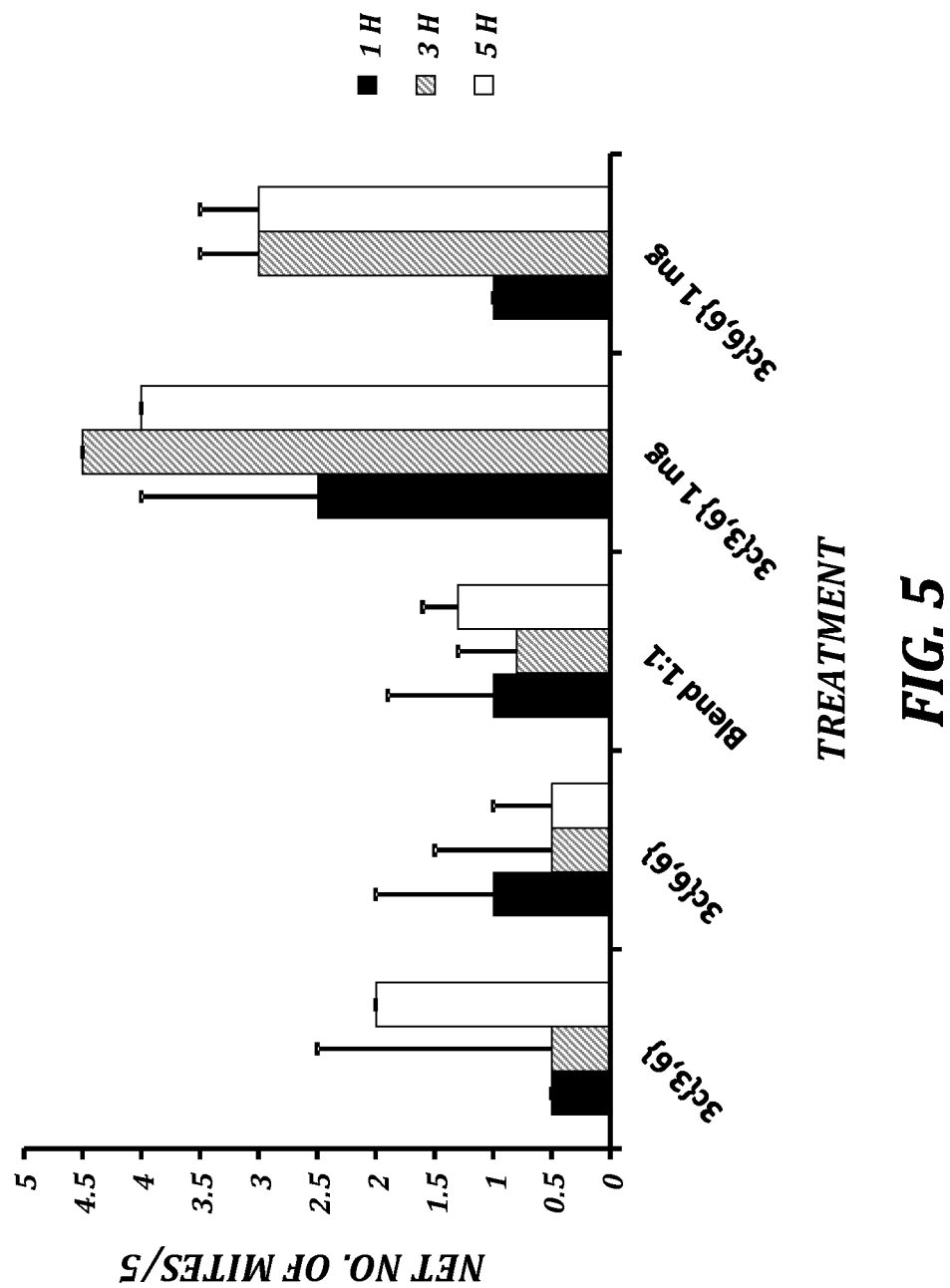
FIG. 5 is a graph of net paralysis+death of mites caused by embodiments of the compounds of the present disclosure, alone or in combination.

Blends of compounds 3c{3,6} and 3c{6,6} were tested. Compounds were tested individually at 0.5 and 1 mg/treatment and in a 1:1 blend at 0.5 mg total. The data also show that compound 3c{3,6} is more active than 3c{6,6}. Referring to FIG. 5, the net paralysis+death of mites caused by compound 3c{3,6} and 3c{6,6} alone or in combination at 0.5 mg, or at 1 mg alone is shown. The paired blank value has been subtracted from that of each treatment. Bars represent the average of 2 replicates±the range.

Mite Paralysis/Death in the Absence of Bees

Compounds 3c{3,6}, 3c{6,6} were tested on mites in the absence of bees, alone and as a 1:1 blend. Mite paralysis and death were checked every 30 min, up to 4.5 h after initial exposure. Four doses were tested: 0.2, 0.5, 1 and 10 mg. Compound 3c{3,6} showed more activity that 3c{6,6}. At the highest doses (1 and 10 mg), compound 3c{3,6} showed 100% of mite paralysis or death, and the lower doses also showed activity (80% paralysis+death at 4.5 h for 0.5 mg and 40% for 0.2 mg). In contrast, compound 3c{6,6} showed no activity for the lower doses, but 100% mite paralysis+death at 10 mg, after 4.5 h of treatment.

Colony Test

Compound 3c{3,6} has been added (as a solid in sachets) four times. After each addition, there was a spike in the number of mites found on the bottom board per day. Mites found were mostly dead; a few were sometimes seen wiggling their front legs, much like in the paralysis assays. Many of the mites (~50%) were white or light brown, some smaller than adult female *Varroa*. The Porapak at the center of the cluster contained 193 ng of 3c{3,6}, and the Porapak at the edge of the cluster contained 148 ng of 3c{3,6}, indicating that the compound is evaporating and spreading within the hive.

Example 4. Partition Assays

Figure 6:
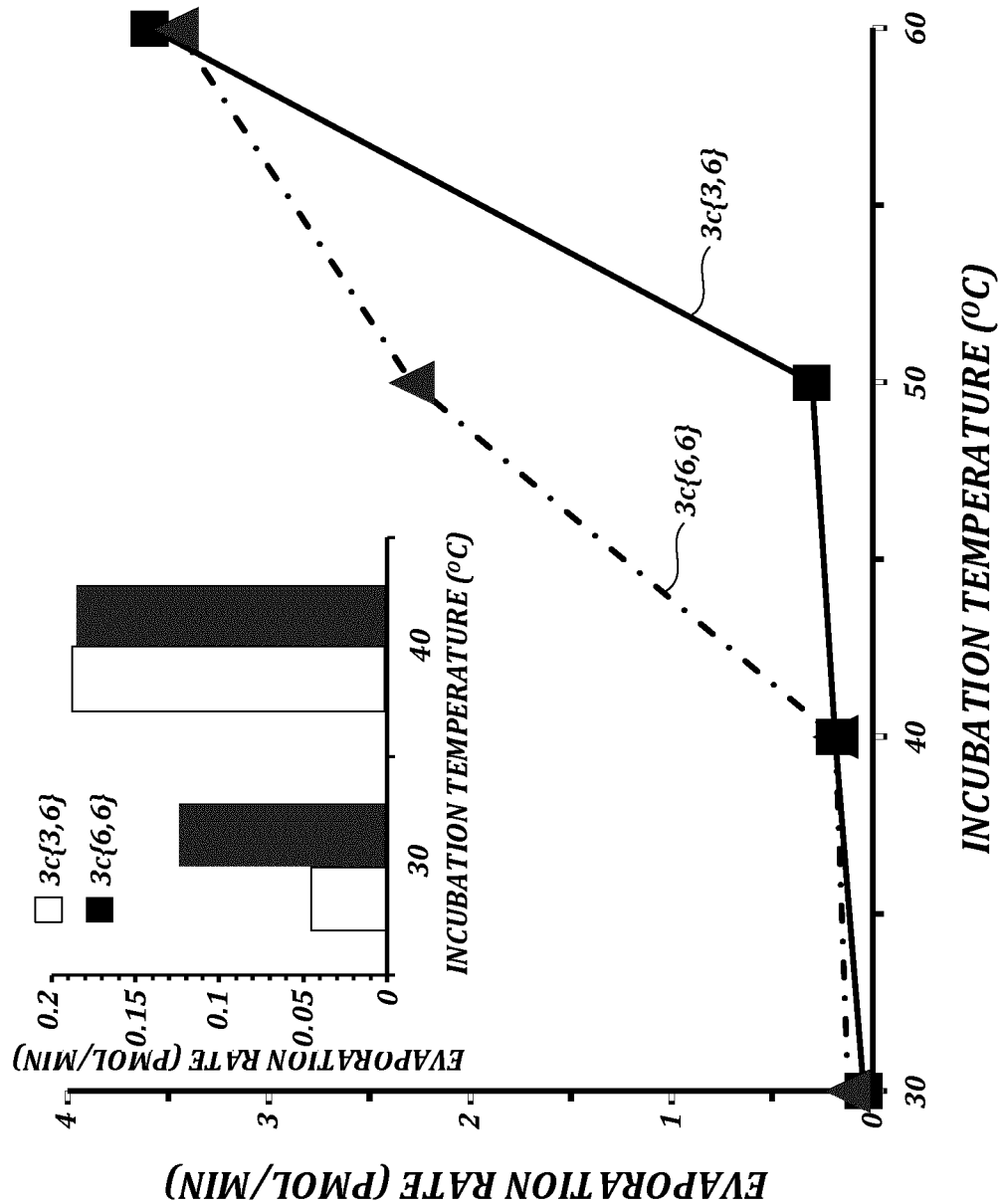
FIG. 6 is a graph of the rates of evaporation of embodiments of compounds of present disclosure in a closed jar fitted with a septum. The inset shows the evaporation rates at 30° C. and 40° C.
Figure 7A:
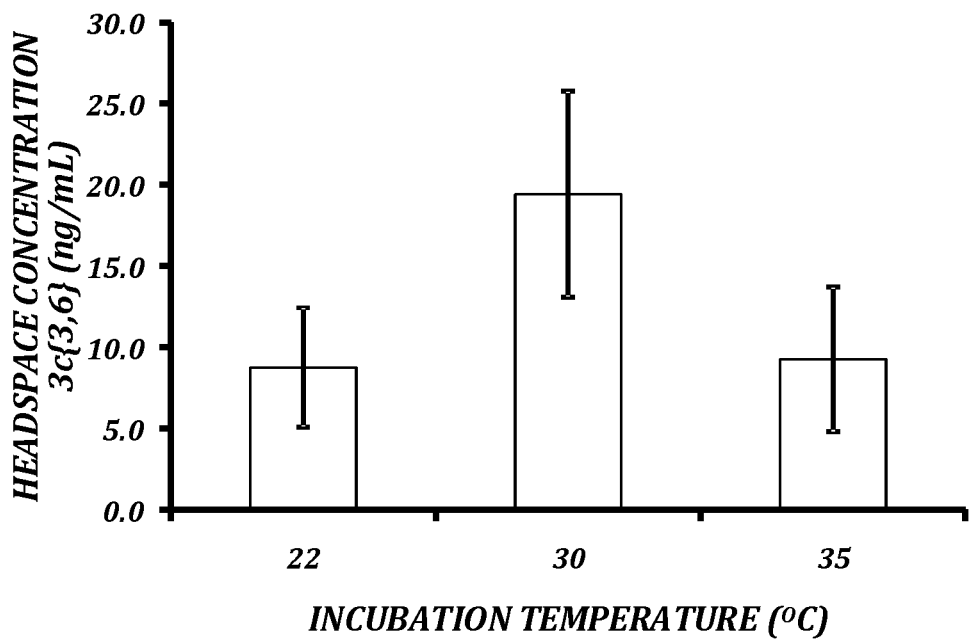
FIG. 7A is bar graph showing the evaporation characteristics of a compound of the present disclosure.
Figure 7B:
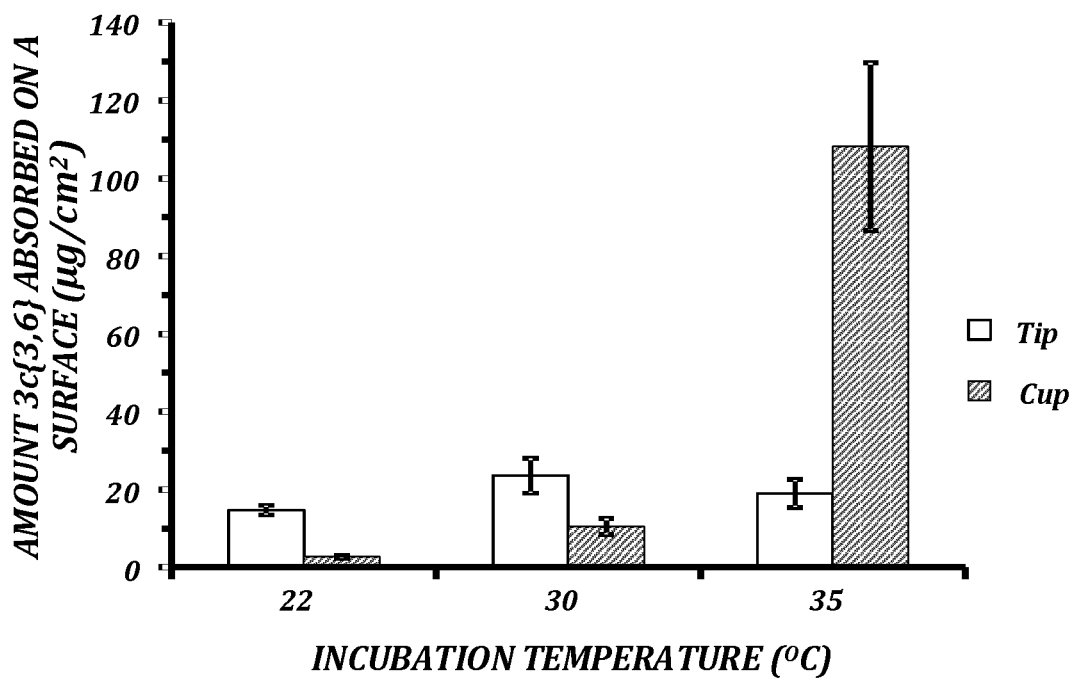
FIG. 7B is bar graph showing the partition characteristics of a compound of the present disclosure.
Figure 7C:
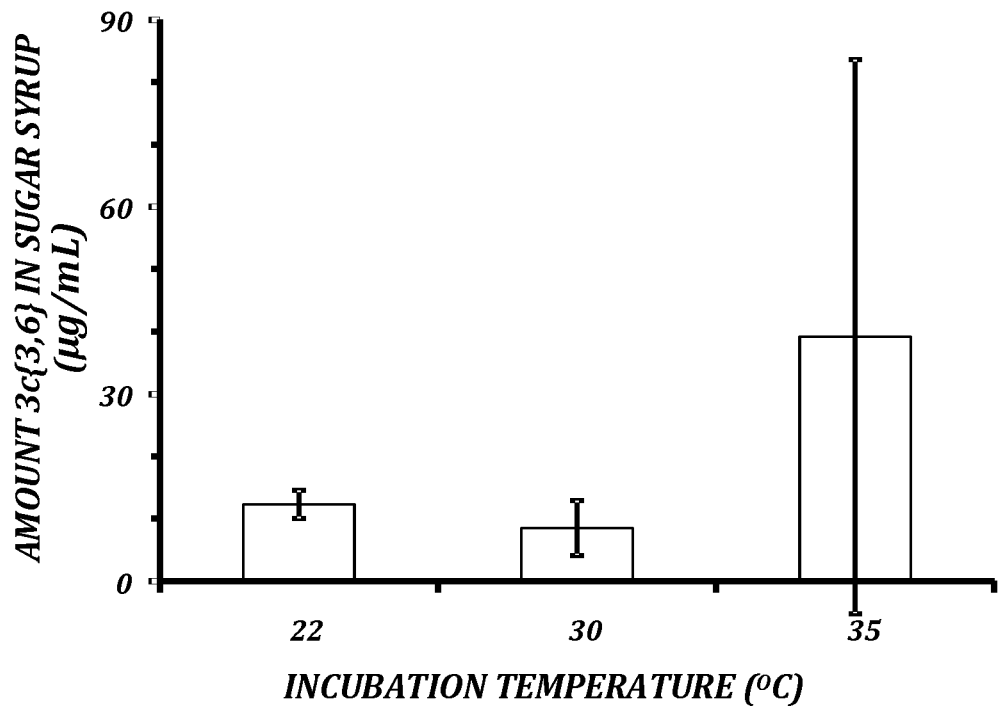
FIG. 7C is bar graph showing the partition characteristics of a compound of the present disclosure.
Figure 7D:
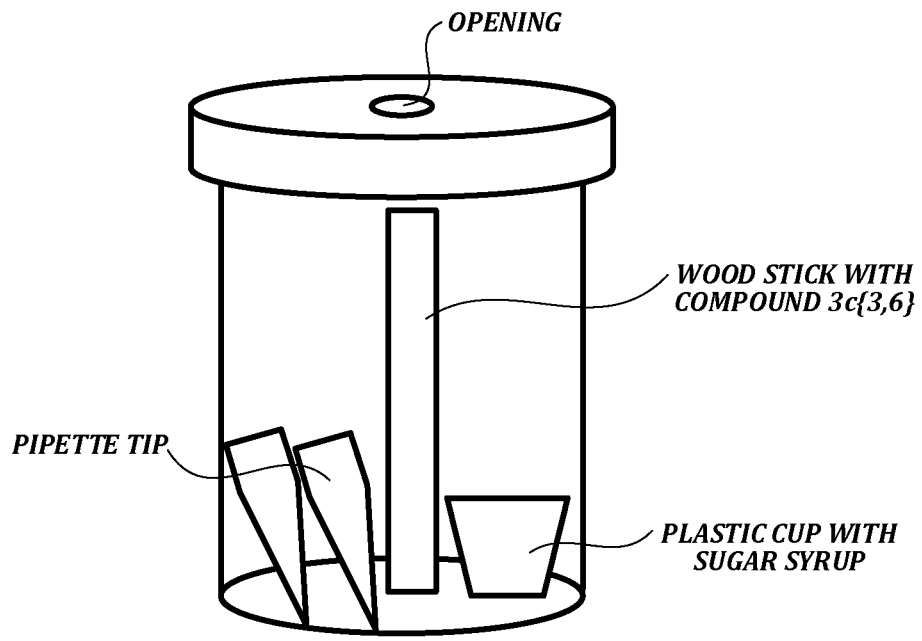
FIG. 7D is a drawing of a representative partition experimental setup with an embodiment of a compound of the present disclosure.

Referring to FIG. 6, the rates of evaporation of compounds 3c{3,6} or 3c{6,6} placed in a closed jar fitted with a septum are shown. The inset shows the evaporation rates at 30 and 40° C. Referring to FIGS. 7A-7D, a partition experiment in 2 L glass jars was performed with an opening (0.5 cm diameter) in the lid. Referring to FIG. 7D, each jar contained one wooden stick coated on both sides with compound 3c{3,6} (500 mg total), two polypropylene pipette tips and a polyethylene cup with 5 mL of sugar syrup (water:sugar 1:1). The setup mimics a bee hive, with a small opening for ventilation, dense hydrophobic wax surfaces (mimicked by the tips), porous hydrophobic surfaces such as wax cappings (mimicked by the plastic cup) and honey (mimicked by the sugar syrup). The wooden stick with the compound did not come in direct contact with the tips or the cup. The experiment was set up in triplicate. Headspace concentration of compound 3c{3,6} was measured every day for 8-9 days, and the average headspace concentration of all days is given in FIG. 7A for each temperature. At the end of the incubation period, the tips were rinsed with organic solvent (hexane:ethyl acetate 4:1) with 1,4-dimethoxybenzene as an internal standard. The sugar syrup was taken out of the cup and extracted, and the cup was also rinsed with solvent. The amount of compound 3c{3,6} that adsorbed on the tips and the cup is shown in FIG. 7B. The amount partitioned into the sugar syrup is shown in FIG. 7C.

Example 5. Effect of Compounds 3c{3,6} and 3c{6,6} and their Combination on *Varroa* Death, Paralysis Assays were done in 9 cm glass Petri dishes. A 2.5×2.5 cm piece of Parafilm was stuck to the lid of the dish, in the middle. 120 µL water were put on filter paper in the middle of the plate. The Parafilm received 10 µL of hexane, either pure (controls) or with the compound (treatments). The bottom of the dish received one freshly thawed nurse and one freshly thawed forager, placed at opposite sides. One mite was placed between the nurse and the forager, the lid was closed and groups of dishes were placed in an incubator at 30° C. Observation times were at 3 h, 5 h and 20 h. Mites were scored for whether the mite could move normally, was paralyzed (had difficulty moving) or dead (not moving). Four types of experiment were performed in the dishes: i) dose response assays with a single compound at different doses of compound on the Parafilm (1 ng, 10 ng, 100 ng, 1 µg, 10 µg, 100 µg, 1 mg) an assay with blends of compounds 3c{3,6} and 3c{6,6} (pure or 1:1 blend) at 0.5 mg and 1 µg doses.

Referring to FIGS. 8A-8C, an additive effect on mites death+paralysis of the two compounds at 500 µg but not at 1 µg. At dose of 1000 µg the effect was not detected, probably due to overload. The blend increased both the death+paralysis. The effect of different doses of 3c{3,6}, 3c{3,6} alone and together on *Varroa* paralysis and death after 1 h (FIG. 8A), 3 h (FIG. 8B), and 5 hours (FIG. 8C). The results are percentage of nine mites in each group. Both 3c{3,6} and 3c{6,6} alone are acaricidal, with 3c{3,6} being more potent.

Example 6. Behavioral Dose Response Bio-Assays of *Varroa* Mites

Three synthetic compounds 3c{3,6}, 3c{6,6} and 3b{2,2} were tested for their effects on *Varroa* mites choice of fresh-killed nurse or forager bees in petri-dishes. The compounds produce a clear paralyzed/killed effect on the mites at high concentrations (≥100 µg). 3c{3,6} was the most active compound with 100% mortality at 1 mg. Mixture ratios of 3c{3,6} and 3c{6,6} were tested with the best combination found at 25:75 that produces 100% mortality on *Varroa* mites at 1 mg.

Foragers were collected at the entrance of one or more honey bee hives by aspiration into a jar, when bees were flying back to the colony. Foragers carrying pollen on their legs were observed at the beginning of the collection period, but they became rare or less frequent by the end.

Initially, nurses were collected from an open brood frame of a honey bee hive. Bees apparently attending the brood were targeted for collection. As time passed and temperatures started to drop no open brood was observed, therefore subsequent collections targeted bees around sealed brood. At the end of the sampling period no sealed brood was present, so bees taken from the middle frame of a brood chamber were considered nurses.

Both foragers and nurses were immediately transferred to individual plastic cages (118×98×81 mm: H×W×D), fed with syrup (2:1) and kept overnight in an incubator at 30° C. and 70% RH. Next day, cages were inspected for any dead bees to be removed before freeze killing the bees on dry ice.

For *Varroa* mite collection, adult bees were taken from the brood chamber's central frames of a mite-infested hive using a glass jar. Bees were fed with syrup (2:1), and kept in an incubator at 30° C. and 70% RH until needed. First collections were made from frames with open and sealed brood, later only from sealed brood frames.

Mite-infested bees in the glass jar were dusted with icy sugar and shaken over a large plastic weighing boat. Dislodged *Varroa* were immediately transferred with a fine paint brush to a wet filter paper in a plastic petri dish to avoid desiccation. Individual mites were placed then onto the middle of a glass petri dish bottom (10 cm diameter) with a fresh freeze-killed forager or nurse bee on opposite sides of the plate. Synthesized compounds were applied onto a 1 cm² Parafilm square attached to the center of the petri dish cover's inner face, Hexane was used as control.

The bio-assays with a forager and a nurse bee, *Varroa* mite, and synthesized compounds were set in glass petri dishes placed into an incubator at 30° C. and 70% relative humidity. All assays had a minimum of five replicates and were repeated twice. Mite paralysis and death were recorded after 3 h and 5 h.

Figure 9:
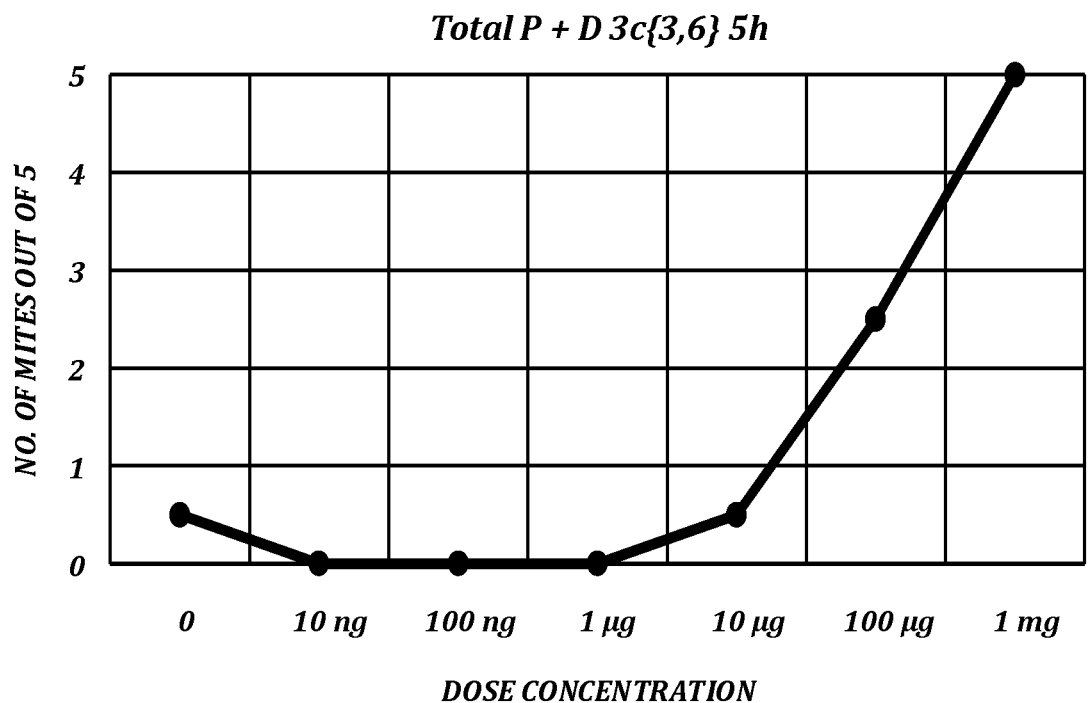
FIG. 9 is a graph of an average from two assays (5 replicates each) of the total number of mites paralyzed and dead when exposed to different concentrations of an embodiment of a compound of the present disclosure.

Compound 3c{3,6}: referring to FIG. 9, mites were paralyzed or killed by the compound at doses ≥10 μg with half of the mites dead at 100 μg (FIG. 9) and total effectivity at 1 mg.

Figure 10:
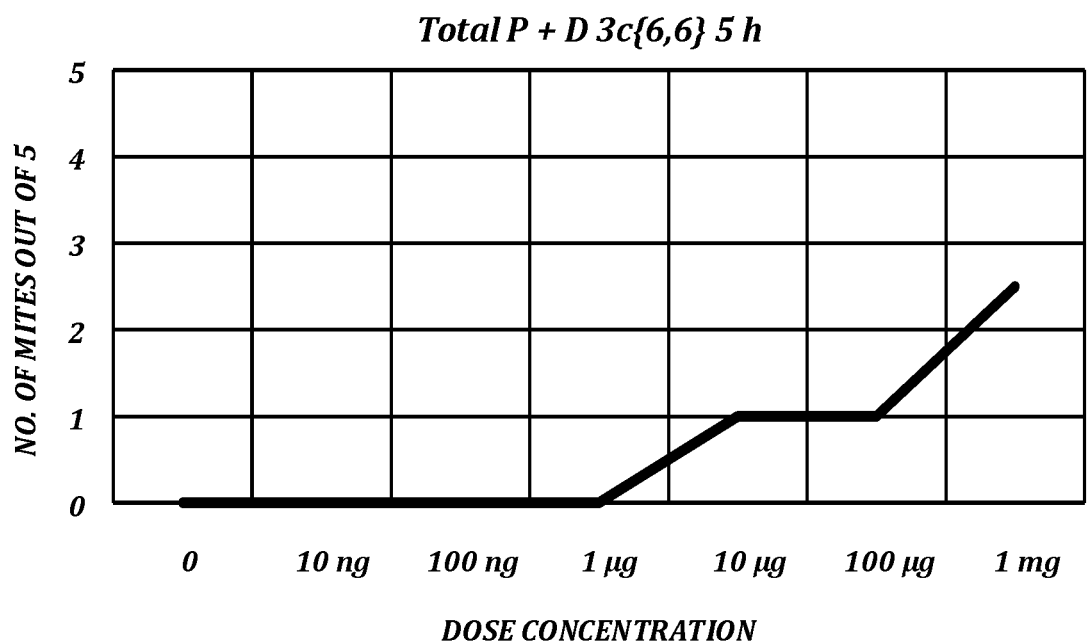
FIG. 10 is a graph of an average from two assays (5 replicates each) of the total number of mites paralyzed and dead when exposed to different concentrations of an embodiment of a compound of the present disclosure.

Compound 3c{6,6}: referring to FIG. 10, mites were paralyzed or killed by the compound at doses ≥10 μg reaching 50% mortality at 1 mg.

3c{3,6} was the most active of the three compounds paralyzing/killing all mites at 1 mg dose, while 3c{6,6} and 3b{2,2} produced 50% paralysis/mortality at that concentration. The same effect on mite paralysis/dead of pure 3c{3,6}(100:0) was obtained when a 25:75 mixture with 3c{6,6} was used, where a 25:75 mixture of 3c{3,6} to 3c{6,6} produced 90% of mite paralysis/dead at 1 mg concentration.

While illustrative embodiments have been illustrated and described, it will be appreciated that various changes can be made therein without departing from the spirit and scope of the disclosure.

The invention claimed is:

1. A method of killing *Varroa destructor*, comprising:
applying an effective amount of a first acaricidal compound selected from

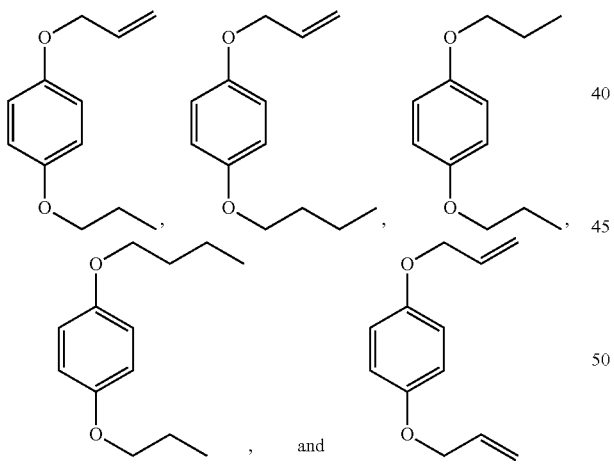

to a *Varroa destructor*-infected honey bee population for a period of at least 3 hours; and
killing the *Varroa destructor* by an amount of at least 50%.

2. The method of claim 1, comprising applying an effective amount of the first acaricidal compound to a *Varroa destructor*-infected honey bee population for a period of at least 14 days.

3. The method of claim 1, comprising applying an effective amount of the first acaricidal compound to a *Varroa destructor*-infected honey bee population for a period of 14 to 28 days.

4. The method of claim 1, wherein the first acaricidal compound selectively kills *Varroa destructor*, does not kill or injure honey bees, or both selectively kills *Varroa destructor* and does not kill or injure honey bees.

5. The method of claim 1, wherein the effective amount of the first acaricidal compound provides from 5 ng to 25 ng of the first acaricidal compound per cm³ of a headspace volume in a honey bee colony enclosure over a period of 3 hours or more and/or 28 days or less.

6. The method of claim 1, wherein applying the effective amount of the first acaricidal compound to a *Varroa destructor*-infected honey bee population comprises applying the first acaricidal compound to a honey bee colony enclosure.

7. The method of claim 1, wherein the first acaricidal compound is

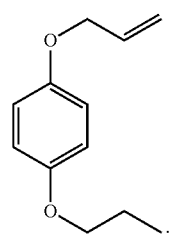

8. The method of claim 1, wherein the first acaricidal compound is

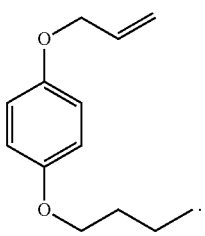

9. The method of claim 1, wherein the first acaricidal compound is

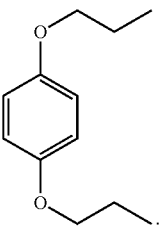

10. The method of claim 1, wherein the first acaricidal compound is

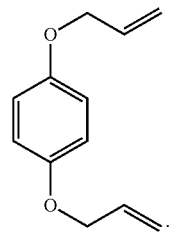

11. The method of claim 1, further comprising applying a second acaricide comprising an organic acid.

12. The method of claim 1, further comprising applying a second acaricide selected from thymol, eucalyptol, camphor, menthol, methyl salicylate, and any combination thereof.

13. The method of claim 1, further comprising applying a compound that alters host choice behavior of *Varroa destructor* selected from 1,3-dialkoxybenzene, 1-ethoxy-5-(2'ethoxyethyl)cyclopent-2-ene, 1-butoxy-5-(2'methoxyethyl)cyclopent-2-ene, or any combination thereof.

14. A method of killing *Varroa destructor*, comprising:
applying an effective amount of a compound of Formula 3c{3,6} to a *Varroa destructor*-infected honey bee population for a period of at least 3 hours; and killing the *Varroa destructor* by an amount of at least 50%.

15. The method of claim 14, comprising applying an effective amount of the compound of Formula 3c{3,6} to a *Varroa destructor*-infected honey bee population for a period of at least 14 days.

16. The method of claim 14, wherein the effective amount of the compound of Formula 3c{3,6} provides from 5 ng to 25 ng of the compound per $cm^3$ of a headspace volume in a honey bee colony enclosure over a period of 3 hours or more and/or 28 days or less.

17. The method of claim 14, wherein the compound having Formula 3c{3,6} selectively kills *Varroa destructor*, does not kill or injure honey bees, or both selectively kills *Varroa destructor* and does not kill or injure honey bees.

18. The method of claim 14, further comprising applying an acaricide comprising an organic acid.

19. The method of claim 14, further comprising applying an acaricide selected from thymol, eucalyptol, camphor, menthol, methyl salicylate, and any combination thereof.

20. The method of claim 14, further comprising applying a compound that alters host choice behavior of *Varroa destructor* selected from 1,3-dialkoxybenzene, 1-ethoxy-5-(2'ethoxyethyl)cyclopent-2-ene, 1-butoxy-5-(2'methoxyethyl)cyclopent-2-ene, or any combination thereof.

* * * * *